(12) United States Patent
Landgraf et al.

(10) Patent No.: US 10,362,467 B2
(45) Date of Patent: Jul. 23, 2019

(54) ENHANCED WIRELESS COMMUNICATION FOR MEDICAL DEVICES

(71) Applicant: Eko Devices, Inc., Berkeley, CA (US)

(72) Inventors: Connor Landgraf, San Francisco, CA (US); Eugene Gershtein, Redwood City, CA (US); Tyler Crouch, San Francisco, CA (US)

(73) Assignee: EKO Devices, Inc., Berkeley, CA (US)

( * ) Notice: Subject to any disclaimer, the term of this patent is extended or adjusted under 35 U.S.C. 154(b) by 0 days.

(21) Appl. No.: 16/020,054

(22) Filed: Jun. 27, 2018

(65) Prior Publication Data
US 2018/0324568 A1 Nov. 8, 2018

Related U.S. Application Data

(63) Continuation of application No. PCT/US2017/067337, filed on Dec. 19, 2017, which
(Continued)

(51) Int. Cl.
*A61B 5/04* (2006.01)
*A61B 5/00* (2006.01)
(Continued)

(52) U.S. Cl.
CPC ............... *H04W 4/80* (2018.02); *A61B 5/002* (2013.01); *A61B 5/0006* (2013.01);
(Continued)

(58) Field of Classification Search
CPC ....... A61B 5/0006; A61B 5/02; A61B 5/0402; H04W 4/008
See application file for complete search history.

(56) References Cited

U.S. PATENT DOCUMENTS 4,802,222 A * 1/1989 Weaver .................. H03G 7/007
375/240
5,657,398 A 8/1997 Guilak
(Continued)

OTHER PUBLICATIONS

PR Newswire. Smart Heart Monitor Keeps the Cardiologist a Heartbeat Away. MPO. (Jun. 7, 2017) retrieved from https://www.mpo-mag.com/contents/view_breaking-news/2017-06-07/smart-heart-monitor-keeps-the-cardiologist-a-heartbeat-away.
(Continued)

*Primary Examiner* — David Bilodeau
(74) *Attorney, Agent, or Firm* — Brad Bertoglio; Intelink Law Group PC

(57) ABSTRACT

Methods and apparatuses for wireless communication between medical devices are provided. In some embodiments, commodity low power, low bandwidth communication protocols may be utilized to simultaneously convey multiple signals with high fidelity and reliability. For example, cardiac sound data and ECG data may be compressed using a common ADPCM component and inserted into a common BLE packet structure. Command-control data may also be inserted. Where required command-control data reporting frequency is less than the packet frequency, header bits may be utilized to convey multiple types of command-control data in a given packet byte position. Rolling packet sequence values may be inserted into the common packet structure, for use by receiving devices to identify link integrity failures.

27 Claims, 3 Drawing Sheets

Related U.S. Application Data is a continuation of application No. 15/384,506, filed on Dec. 20, 2016, now Pat. No. 9,736,625.

(51) Int. Cl.
| | | |
|---|---|---|
| *A61B 5/0402* | (2006.01) | |
| *H04W 4/80* | (2018.01) | |
| *A61B 7/00* | (2006.01) | |
| *H04W 4/70* | (2018.01) | |
| *H04W 4/38* | (2018.01) | |
| *G06F 19/00* | (2018.01) | |
| *G16H 40/63* | (2018.01) | |

(52) U.S. Cl.
CPC ........ *A61B 5/0402* (2013.01); *A61B 5/04017* (2013.01); *A61B 7/00* (2013.01); *H04W 4/38* (2018.02); *H04W 4/70* (2018.02); *G06F 19/30* (2013.01); *G16H 40/63* (2018.01); *Y02D 70/144* (2018.01)

(56) References Cited

U.S. PATENT DOCUMENTS

| | | | | |
|---|---|---|---|---|
| 6,370,423 | B1* | 4/2002 | Guerrero | A61B 5/044 600/513 |
| 2005/0078533 | A1 | 4/2005 | Vyshedskiy et al. | |
| 2007/0208233 | A1 | 9/2007 | Kovacs | |
| 2008/0167566 | A1* | 7/2008 | Unver | A61B 5/0006 600/513 |
| 2013/0116584 | A1 | 5/2013 | Kapoor | |
| 2014/0328210 | A1 | 11/2014 | Knaappila | |
| 2016/0014550 | A1* | 1/2016 | Chiddarwar | H04W 52/0216 455/41.2 |
| 2016/0100817 | A1 | 4/2016 | Hussain | |
| 2016/0144192 | A1 | 5/2016 | Sanghera et al. | |
| 2017/0097981 | A1* | 4/2017 | Kalevo | H04N 19/46 |

OTHER PUBLICATIONS

PCT International Search Report, International application No. PCT/US18/021964 (dated May 30, 2018).

Dan, Chunmei et al., "Playing and Acquiring Heart Sounds and Electrocardiogram Simultaneously Based on LabVIEW", 2008 World Automation Congress, Hawaii, HI, 2008, pp. 1-4 (http://ieeexplore.ieee.org/stamp/stamp.jsp?tp=&arnumber=4699304&isnumber=4698939).

PCT International Search Report, International application No. PCT/US17/67337 (dated Jan. 30, 2018).

PCT Written Opinion of the International Searching Authority, International Application No. PCT/US17/67337 (dated Jan. 30, 2018).

* cited by examiner

ENHANCED WIRELESS COMMUNICATION FOR MEDICAL DEVICES

TECHNICAL FIELD

The present disclosure relates to medical devices utilizing wireless electronic communications. More specifically, this disclosure relates to methods and apparatuses for enhancing wireless communications in medical device applications, such as wireless cardiac sensors.

BACKGROUND

Use of wireless communications techniques for electronic devices is becoming increasingly popular. Wireless devices provide convenience and ease of use. Bluetooth has become particularly prevalent as a wireless communications protocol. It provides versatile mechanisms for transmitting digital signals over short distances with very low power consumption. Bluetooth has become a ubiquitous standard amongst mobile phones, tablet computers, personal computers, wireless headphones, automobiles, and a wide variety of other device types. As a result, Bluetooth devices are readily interoperable with other electronic devices. Meanwhile, high production volumes result in ready availability and relatively low cost for transceiver chipsets and circuit boards, further reinforcing the widespread adoption of the standard.

Bluetooth Low Energy ("BLE") is a subprotocol defined within the Bluetooth 4.0 protocol, that enables highly energy-efficient transfer of data between a client device (e.g. a sensor) and a server device (e.g. a mobile phone or personal computer). BLE can be particularly valuable for battery-operated devices, for which minimizing power consumption may be critical.

While the prevalence of Bluetooth and power-efficiency of BLE provide many advantages, some device types, particularly in the context of medical instrumentation, give rise to communication requirements that may not be well-satisfied by standard Bluetooth implementations. For example, many types of instrumentation may require transmission of multiple signal types, which would traditionally be conveyed by multiple wires or multiple wireless radios. However, consumer electronic devices may be limited in the number of radios provided, while sensors with multiple radios may require greater power consumption, resulting in larger batteries and/or worse battery life. Meanwhile, BLE bandwidth limitations may impact sensor performance. For example, while humans can typically perceive sounds ranging from about 20 Hz to about 20 kHz, BLE as a protocol does not have enough bandwidth to transmit the entirety of the human audio spectrum, due to small packet size and slow packet speed. Traditional Bluetooth and BLE implementations may be particularly disadvantageous or limiting for medical devices such as wireless cardiac devices.

SUMMARY

Improved implementations of BLE-based wireless communication protocols can provide high levels of performance in wireless medical device applications, while still enabling use of commodity Bluetooth transceiver hardware and commodity host electronic devices.

In some embodiments, a method is provided for transmitting cardiac data from a wireless sensor to a host device. Cardiac sound data and ECG data are received at a wireless sensor, such as via onboard transducers digitizing audio and electrical signals sensed on a patient. The cardiac sound and ECG data can be filtered, such as via application of a digital lowpass filter to cardiac sound data to attenuate frequency components above approximately 2 kHz. The cardiac sound data and ECG data are compressed, such as through application of the data to an adaptive differential compression component. In some embodiments, a common adaptive differential compression component can be applied to both the cardiac sound data and the ECG data. The compressed cardiac sound data and compressed ECG data can be combined into a common packet structure, and transmitted from the wireless sensor to the host device.

The common packet structure may also include command-control data. In embodiments where the packet frequency is greater than the required frequency of command-control data reporting, command-control data may include a header bit indicating one of multiple command-control data content types with which an associated command-control value is associated—thereby reducing the number of bits that must be allocated to command-control data within the packet structure.

The common packet structure may also include mechanisms to identify wireless communication link integrity problems. A packet sequence value, such as a rolling four-bit value, can be inserted into each packet by the transmitting device, such as a cardiac sensor. The receiving device, e.g. the host device, can decode the packet sequence value towards ensuring that sequentially-received packets have sequential packet sequence values. In the event that the receiving device identifies a gap in rolling packet sequence values, the receiving device may determine the existence of a failure of the wireless communication link integrity. Such a failure may then be conveyed to a user via, e.g., displaying a warning indicia on a host device user interface.

DETAILED DESCRIPTION OF THE DRAWINGS

Figure 1:
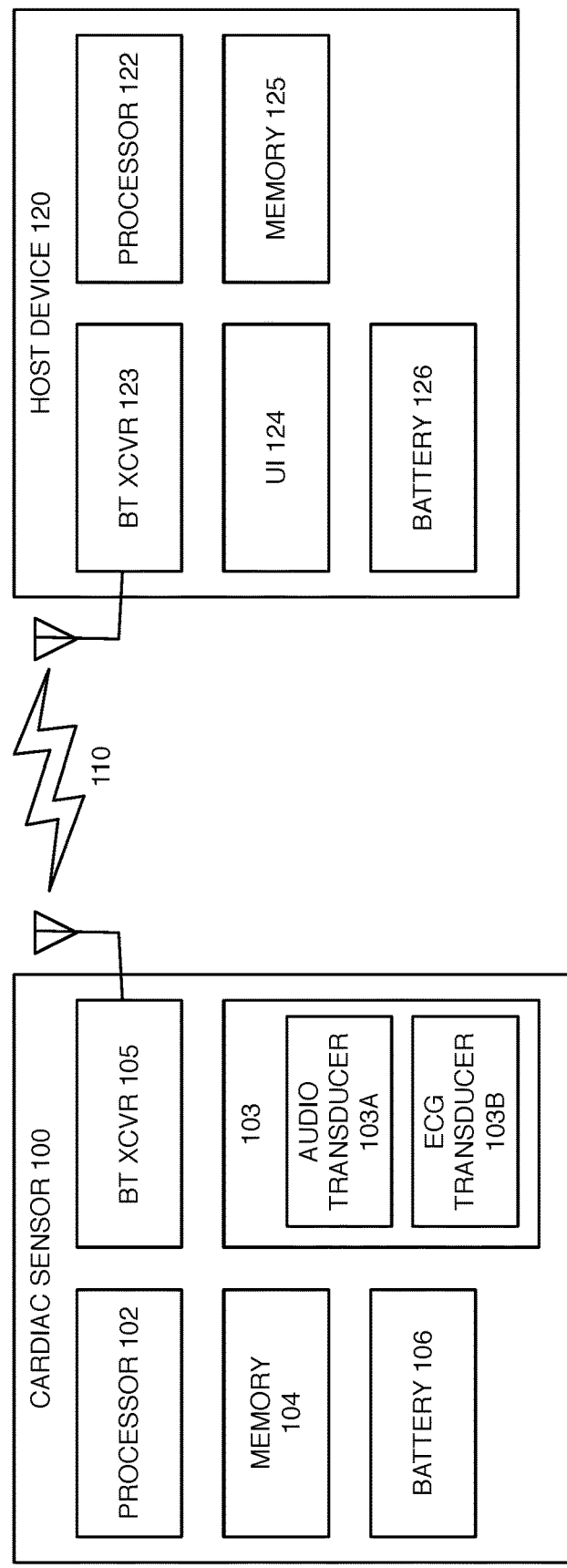
FIG. 1 is a schematic block diagram of a medical instrumentation environment including a wireless cardiac sensor and host device.

While this invention is susceptible to embodiment in many different forms, there are shown in the drawings and will be described in detail herein several specific embodiments, with the understanding that the present disclosure is to be considered as an exemplification of the principles of the invention to enable any person skilled in the art to make and use the invention, and is not intended to limit the invention to the embodiments illustrated.

Techniques are described that can be used to effectively transmit medical device data, particularly heart diagnostic data, via a low-power, low-bandwidth wireless communications protocol such as Bluetooth Low Energy. Several techniques described hereinbelow can be applied individually or in combination.

FIG. 1 illustrates a typical operating environment in which embodiments can be employed. Cardiac sensor 100 is a wireless heart monitor capable of detecting multiple types of diagnostic data, including heart sounds and ECG electrical recordings. Sensor 100 includes microprocessor 102 for processing and storing data from transducers 103 into memory 104. Sensor transducers 103 can include audio transducer 103A, for auscultation such as recording of heart sounds, and ECG transducer 103B, for monitoring of cardiac electrical activity. Bluetooth transceiver 105 is in operable communication with processor 102 in order to convey data to and from remote electronic devices, such as host device 120. Battery 106 is a rechargeable battery supplying power to sensor 100. In order to maximize the duration between required charges, and minimize the size, weight and expense of sensor 100, sensor 100 is designed for low power consumption during operation.

Sensor 100 communicates via wireless data connection 110 with host device 120. Host device 120 may preferably be a standard, commodity mobile wireless computing device, such as a smartphone (e.g. Apple iPhone™), tablet computer (e.g. Apple iPad™), or laptop computer. Host device 120 includes microprocessor 122 for processing and storing data. Bluetooth transceiver 123 enables wireless communication between processor 122 and external devices, such as sensor 100. Host device 120 further includes user interface components 124 (such as a touchscreen), memory 125 for data storage, and battery 126. While illustrated as a mobile device in the embodiment of FIG. 1, in other embodiments, host device 120 could alternatively be selected from amongst other types of computing devices having a Bluetooth transceiver, such as a personal computer or a central sensor monitoring station.

The BLE protocol may be desirable for implementation of wireless communications link 110, in order to minimize energy consumption during operation and therefore extend the battery life of sensor 100 and host device 120. However, BLE, as commonly implemented, presents significant limitations in a wireless cardiac sensor environment. One such limitation is bandwidth. Common mobile devices 120 have limitations in packet rate utilizing the BLE protocol for communications link 110. For example, some mobile phones may have a theoretical minimum packet interval at which one BLE packet can be accepted every 5 milliseconds. Exacerbating this limitation is a need in medical applications for high data integrity and reliability. In such embodiments, it may not be desirable to potentially sacrifice data integrity and link reliability by requiring data transmission at or near theoretical maximum packet rates. While decreasing packet rate may provide better packet interval operating margin, bandwidth constraints are even more limiting. With some common consumer mobile devices, it has been found that reliable BLE communications can be maintained sending packets at 8 ms intervals.

BLE also imposes packet size constraints. Moreover, regardless of protocol constraints on packet size, it may be further desirable to reduce packet size in order to reduce power consumption. Meanwhile, in order to implement an effective wireless cardiac sensor providing both auscultation and ECG data, packets will preferably accommodate multiple data streams, such as heart sound audio data from audio transducer 103A, ECG data from transducer 103B, and command-and-control data associated with the operation of cardiac sensor 100 and its interaction with host device 120. Packet efficiency may be critical to use of BLE in such environments.

Figure 2:
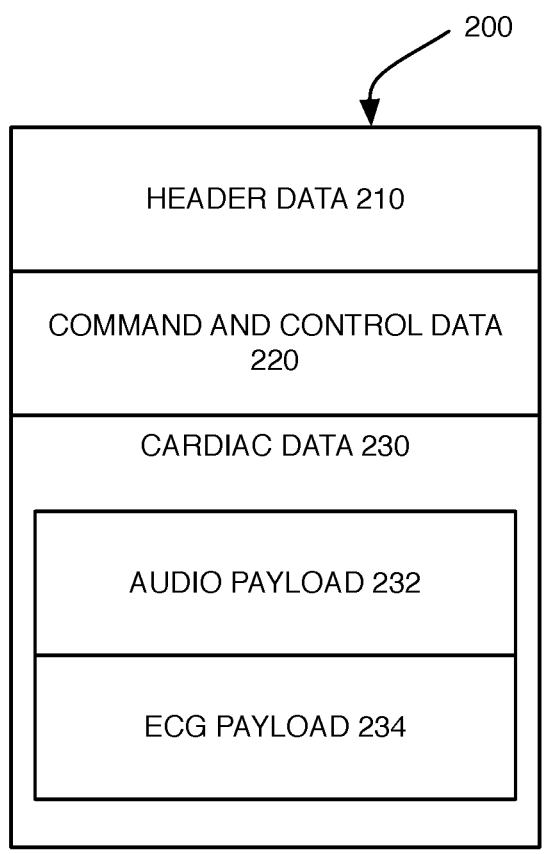
FIG. 2 is a schematic block diagram of a wireless packet structure.

FIG. 2 illustrates an optimized BLE packet structure that may be utilized in communications from cardiac sensor 100 to host device 120. The packet structure of FIG. 2 is optimized to convey multiple types of medical instrument and control data via a relatively low-bandwidth and low-power BLE communication link that can be reliably received by standard smartphones, tablets or other consumer electronic devices. Specifically, the packet structure of FIG. 2 conveys heart sounds, ECG data and command/control data simultaneously, with clinical fidelity, within a single BLE packet, using one standard BLE radio set.

Each packet 200 in FIG. 2 is preferably formed having a byte length provided for by BLE standards, and packet intervals preferably compatible with commodity BLE chipsets and computing devices. Such a data structure may provide an effective bitrate of approximately 20 kbps.

Figure 3:
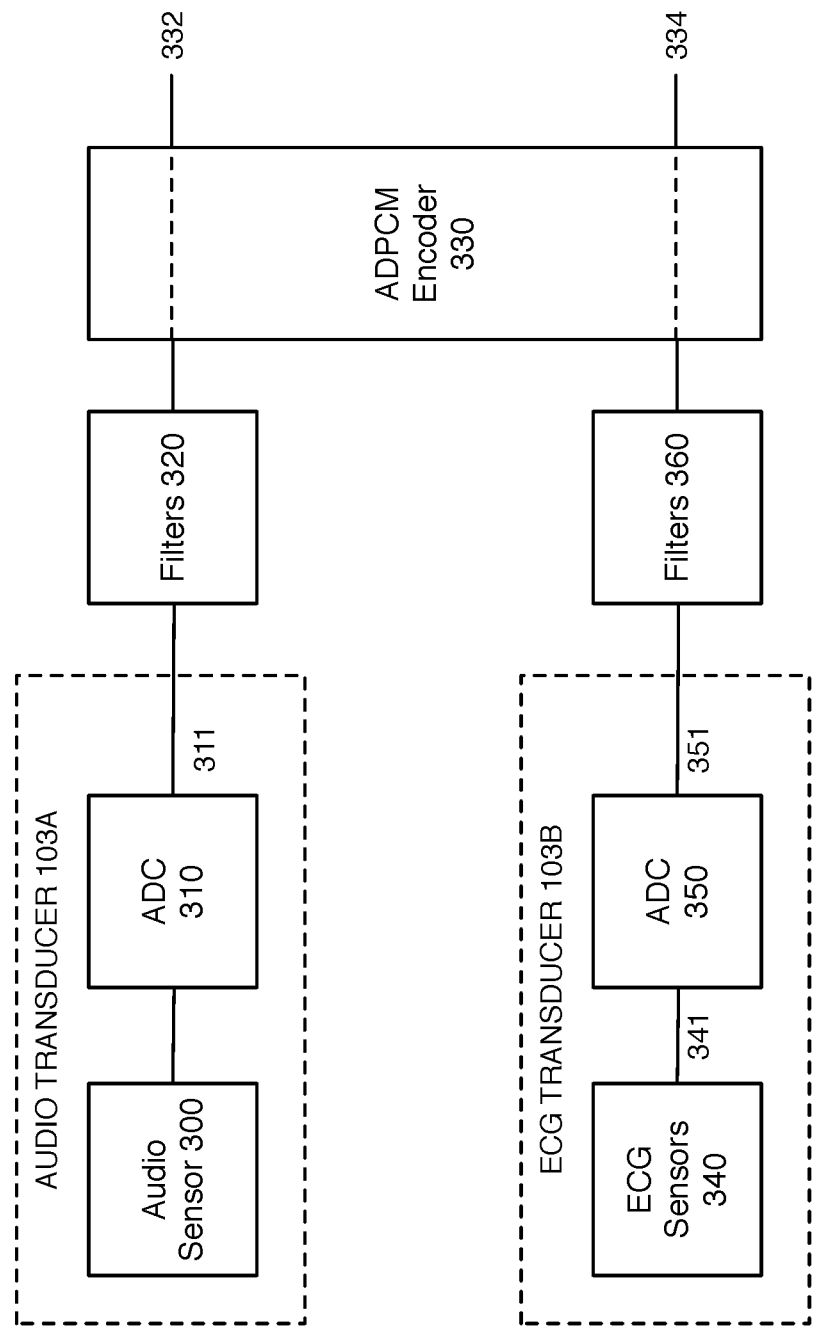
FIG. 3 is a schematic block diagram of a cardiac signal processing chain.

Packet 200 includes header bytes 210, command and control bytes 220, and cardiac data 230. In the illustrated embodiment, cardiac data 230 includes audio payload 232 and ECG payload 234. Audio payload 232 is utilized for transmitting heart sound data recorded by audio transducer 103A. FIG. 3 illustrates a schematic representation of cardiac signal processing components within cardiac sensor 100, which operate to generate data conveyed in the BLE packet structure of FIG. 2. Audio sensor 300 converts an audio signal, such as cardiac auscultation, into an analog electronic signal. Analog-to-digital converter (ADC) 310 samples the output of sensor 300 and generates a digital data stream 311. ADC 310 initially samples acoustic heart sound signals at an approximately 4 kHz sample rate, with 16-bit samples, yielding a 64 kbps audio stream. Audio compression is applied by adaptive differential pulse-code modulation (ADPCM) encoder 330 to yield a 4-bit audio stream 332 at a 4 kHz rate (i.e. one 4-bit sample each 0.25 ms). Therefore, with an 8 ms packet interval, each packet 200 includes audio payload 232 having 32 4-bit audio samples.

Digital filters 320 can be applied to the output 311 of ADC 310 prior to ADPCM encoder 330 in order to reduce artifacts and distortion during the ADPCM compression process. In particularly, filters 320 will include strong low-pass filters to eliminate or drastically attenuate high frequency components above the 2 kHZ range. It has been determined that frequency range limitations imposed by aggressive pre-filtering of cardiac auscultation sounds before ADPCM compression is preferable for purposes of human medical diagnostics, as compared to less aggressive filtering accompanied by potential introduction of compression noise and artifacts by ADPCM encoder 330.

Another advantage of the packet structure of FIG. 2, particularly given limitations on packet interval in common smartphones and other mobile devices that may be utilized as host device 120, is that it combines heart sound and ECG data within a single BLE packet. FIG. 3 further illustrates a schematic representation of an ECG data pipeline that may be implemented on cardiac sensor 100. In use, ECG sensors 340 are connected to a patient, and output electrical signals 341 indicative of a patient's cardiac electrical activity.

Cardiac electrical signals 341 are sampled by analog-to-digital converter 350. In an exemplary embodiment, ADC 350 may generate 16-bit samples at a 500 Hz sampling rate. This yields a digital ECG data stream 351 having a data rate of 8 kbps, to which filter 360 may be applied. Utilizing an 8 ms BLE packet interval, ECG data stream 351 would therefore require 8 bytes within each BLE packet. However, given the amount of packet 200 allocated to cardiac audio data, as described above, it may be desirable to compress the ECG data stream, provided the compression can be achieved without material negative impact on the ECG data fidelity.

It has been determined that the same ADPCM encoder 330 used to encode cardiac audio data, can also be effectively utilized to reduce ECG data bandwidth without significant negative impact on the ECG signal fidelity via strategic specification of sample rate. By selecting a 500 Hz sample rate, measurement differentials between adjacent samples in a typical digitized ECG signal are such that the ECG data stream may be effectively encoded by ADPCM encoder 330 to yield an encoded ECG data stream 334 that reduces the size of ECG payload 234.

In some embodiments, audio sensor 300 and ADC 310 can be implemented within audio transducer 103A, ECG sensors 340 and ADC 350 can be implemented within ECG transducer 103B, with filter 320, filter 360 and encoder 330 being implemented by processor 102. In other embodiments, the elements of FIG. 3 can be distributed differently amongst components such as audio transducer 103A, ECG transducer 103B, processor 102, custom ASICs, GPUs, or other components.

Bandwidth-efficient conveyance of command and/or control data (sometimes referred to as command-control data) may also be important in wireless cardiac sensor and other medical device applications. For command-control data of a nature that the acceptable reporting frequency is less than the packet frequency, it may be desirable for sequential packets to transmit different command-control data content types within the same packet bit positions. A header bit or bits may be utilized to indicate which of multiple types of command-control data is conveyed within associated packet bit positions.

For example, in the context of a wireless cardiac sensor transmitting at an 8 ms packet interval, it may not be necessary to transmit certain command-control data, such as volume level or battery level, at 8 ms intervals. Longer intervals may be sufficient, while still ensuring users perceive a high level of responsiveness. Thus, in the packet structure of FIG. 2, bits within header 210 can be utilized to convey one of multiple content types of command-control data. For example, a header bit may be utilized to indicate whether the data within command and control data 220 reflects a volume level or battery level. Depending on the number of bits required for sufficient command-control data value granularity, and the desired frequency of command-control data conveyance, in other embodiments, multiple header bits can be utilized to enable greater numbers of command-control data content types to be conveyed within a given packet byte position. For example, in another embodiment, two bits may be used to specify one of four different command-control data content types, with associated bit positions conveying an associated value. In some embodiments, header bits may be conveyed in different byte positions from associated command and control values within packet 200; in other embodiments, header bits and associated command and control values may be conveyed within the same byte position of packet 200, thereby intermixing header data 210 and command and control data 220.

Another important aspect of wireless communications in some medical applications is verifying link integrity. For high risk data such as heart sound and ECG data, it may be desirable for devices to rapidly and reliably alert the user when a data transmission quality problem arises. By effectively identifying data transmission issues, a user can promptly remedy equipment problems and ensure that anomalous results are attributed to instrumentation error rather than the patient being monitored. However, traditional BLE protocols do not provide mechanisms to determine when packets are dropped.

Therefore, the packet of FIG. 2 preferably includes a link integrity verification mechanism integrated within the packet structure. Predetermined bits within header 210 can be allocated to a rolling packet sequence indicator. When transmitted by cardiac sensor 100, processor 102 constructs consecutive packets to increment through a rolling multi-bit packet sequence value. The receiving device 120 can then decode the packet sequence value to verify that consecutive packets are received with sequentially incrementing packet sequence values. In the event that packet sequence values are not sequential in adjacent packets, receiving device 120 can determine that the integrity of link 110 has been compromised, and alert a user to the issue by, e.g., displaying an appropriate warning indicia on user interface 124. The embodiment of FIG. 2 utilizes a rolling packet sequence value that is four bits in length, which in some embodiments may be an optimal tradeoff between minimizing failures to identify link integrity problems (for which longer sequence values are better), and minimizing power consumption and bandwidth attributed to the link integrity verification function (for which shorter sequence values are better).

The previous description of the disclosed embodiments is provided to enable any person skilled in the art to make or use the invention disclosed herein. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein. All references cited herein are expressly incorporated by reference.

The invention claimed is:

1. A method for collecting diagnostic data from a heart of a subject, comprising:
   (a) using a monitoring device comprising an ECG sensor and an audio sensor to measure ECG data and audio data from said heart of said subject;
   (b) inserting both said ECG data and said audio data by said monitoring device into a common packet structure;
   (c) transmitting said ECG data and audio data wirelessly to a computing device separate from said monitoring device using said common packet structure; and
   (d) using said computing device to process said ECG data and audio data to provide an output indicative of said state or condition of said heart of said subject.

2. The method of claim 1, further comprising, prior to (b), compressing said ECG data and said audio data using a common compression component.

3. The method of claim 2, further comprising, prior to (b), filtering said ECG data and said audio data, wherein said filtering comprises attenuating frequency components above 2 kHz.

4. The method of claim 2, further comprising (i) determining that a wireless communication link between said computing device and said monitoring device has been compromised, and (ii) displaying a warning on a user interface of said computing device, which warning is indicative of a compromise in said wireless communication link.

5. The method of claim 2, wherein said ECG data and said audio data are transmitted from said monitoring device to said computing device via a Bluetooth Low Energy communications link.

6. The method of claim 2, in which the step of transmitting said ECG data and audio data wirelessly comprises transmitting via a common transceiver with a packet interval of at least five milliseconds.

7. The method of claim 1, further comprising (i) determining that a wireless communication link between said computing device and said monitoring device has been compromised, and (ii) displaying a warning on a user interface of said computing device, which warning is indicative of a compromise in said wireless communication link.

8. The method of claim 1, further comprising inserting a rolling packet sequence value into said common packet structure.

9. The method of claim 8, further comprising (i) receiving at said computing device a data packet having a non-sequential rolling packet sequence value, and (ii) displaying a warning on a user interface of said computing device, which warning is indicative of a compromise in a wireless communication link between said monitoring device and said computing device.

10. The method of claim 1, wherein said common packet structure comprises command-control data.

11. The method of claim 10, wherein said command-control data comprises two or more types of command-control data content, at least one of which is present at a reporting frequency that is lower than a data packet frequency corresponding to said ECG data and said audio data.

12. The method of claim 10, wherein said command-control data comprises a header value indicative of a content type of said command-control data.

13. The method of claim 1, wherein said ECG data and said audio data are transmitted from said monitoring device to said computing device via radio frequency communication.

14. The method of claim 1, wherein said ECG data and said audio data are transmitted from said monitoring device to said computing device via a Bluetooth Low Energy communications link.

15. The method of claim 1, further comprising storing said ECG data and said audio data on said monitoring device.

16. The method of claim 1, further comprising identifying, by said computing device, a data transmission issue with transmitting said ECG data and said audio data from said monitoring device to said computing device.

17. The method of claim 1, wherein said computing device is a mobile computing device.

18. The method of claim 1, in which the step of transmitting said ECG data and audio data wirelessly comprises transmitting the common packet structure via a Bluetooth Low Energy communications link with a packet interval of at least five milliseconds.

19. The method of claim 18, in which the packet interval is eight milliseconds.

20. The method of claim 1, in which the step of using a monitoring device comprising an ECG sensor and an audio sensor to measure ECG data and audio data from said heart of said subject comprises:

sampling, by the monitoring device, an ECG signal of the subject to yield ECG data comprising 16-bit samples at a sampling rate of 500 Hz;
applying a lowpass filter to the ECG data; and
compressing the ECG data by application of an ADPCM encoder.

21. The method of claim 20, in which the step of using a monitoring device comprising an ECG sensor and an audio sensor to measure ECG data and audio data from said heart of said subject further comprises: compressing the audio data by application of the ADPCM encoder.

22. A method for collecting diagnostic data from a heart of a subject, comprising:
(a) using a monitoring device comprising an ECG sensor and an audio sensor to measure ECG data and audio data from said heart of said subject;
(b) compressing said ECG data and said audio data using a common compression component;
(c) transmitting said ECG data and audio data wirelessly to a computing device separate from said monitoring device; and
(d) using said computing device to process said ECG data and audio data to provide an output indicative of said state or condition of said heart of said subject.

23. The method of claim 22, wherein the common compression component comprises an ADPCM encoder.

24. The method of claim 23, further comprising, prior to step (b), filtering said ECG data and said audio data using a lowpass filter to attenuate frequency components above 2 kHz.

25. The method of claim 22, further comprising (i) determining that a wireless communication link between said computing device and said monitoring device has been compromised, and (ii) displaying a warning on a user interface of said computing device, which warning is indicative of a compromise in said wireless communication link.

26. The method of claim 22, wherein said ECG data and said audio data are transmitted from said monitoring device to said computing device via a Bluetooth Low Energy communications link.

27. The method of claim 22, in which the step of transmitting said ECG data and audio data wirelessly comprises transmitting via a common transceiver with a packet interval of at least five milliseconds.

* * * * *